(12) United States Patent
Park

(10) Patent No.: US 10,758,339 B2
(45) Date of Patent: Sep. 1, 2020

(54) INTRAOCULAR LENS ASSEMBLY

(71) Applicant: LOSEC CO., LTD., Seoul (KR)

(72) Inventor: Kyung Jin Park, Seoul (KR)

(73) Assignee: LOSEC CO., LTD., Seoul (KR)

( * ) Notice: Subject to any disclaimer, the term of this patent is extended or adjusted under 35 U.S.C. 154(b) by 0 days.

(21) Appl. No.: 15/578,199

(22) PCT Filed: Jun. 5, 2015

(86) PCT No.: PCT/KR2015/005671
§ 371 (c)(1),
(2) Date: Nov. 29, 2017

(87) PCT Pub. No.: WO2016/195143
PCT Pub. Date: Dec. 8, 2016

(65) Prior Publication Data
US 2018/0147049 A1 May 31, 2018

(30) Foreign Application Priority Data

May 29, 2015 (KR) .................. 10-2015-0076716

(51) Int. Cl.
*A61F 2/16* (2006.01)
(52) U.S. Cl.
CPC .......... *A61F 2/1613* (2013.01); *A61F 2/1635* (2013.01); *A61F 2/1648* (2013.01); *A61F 2/1694* (2013.01); *A61F 2002/1681* (2013.01)
(58) Field of Classification Search
CPC .................. A61F 2/1613; A61F 2/1648; A61F 2002/1681; A61F 2002/1682;
(Continued)

(56) References Cited

U.S. PATENT DOCUMENTS

| 5,628,798 A * | 5/1997 | Eggleston ............... A61F 2/16 623/6.11 |
| 2005/0085907 A1* | 4/2005 | Hanna .................. A61F 2/1613 623/6.37 |

(Continued)

FOREIGN PATENT DOCUMENTS

| KR | 10-0807940 B1 | 2/2008 |
| KR | 10-2008-0065579 A | 7/2008 |
| KR | 10-2011-0127706 A | 11/2011 |

OTHER PUBLICATIONS

International Search Report for International Patent Application No. PCT/KR2015/005671, dated Jun. 5, 2015.

*Primary Examiner* — Leslie Lopez

(57) ABSTRACT

An intraocular lens assembly configured to effectively transfer movement of a zonule of Zinn to improve performance of an intraocular lens. The intraocular lens assembly is inserted into the eyeball, and includes: an intraocular lens support body (10) configured in a shape of a ring inserted into the capsular sac of the eyeball, and provided with an outer circumferential surface (11) including a first front contact portion (11*a*) and a first rear contact portion (11*b*), and an inner circumferential surface (12) facing the outer circumferential surface (11) and including a second front contact portion (12*a*) and a second rear contact portion (12*b*); a connection means (50) including a deformation facilitating groove (52*c*) provided between a third front contact portion (52*a*) and a third rear contact portion (52*b*) and forming a space spaced apart from the inner circumferential surface (12); and an intraocular lens (30) connected to the connection means.

17 Claims, 8 Drawing Sheets

(58) Field of Classification Search
CPC ...... A61F 2002/169; A61F 2002/16901; A61F 2002/16902; A61F 2/1694
See application file for complete search history.

(56) References Cited

U.S. PATENT DOCUMENTS

| | | | |
|---|---|---|---|
| 2010/0016963 A1* | 1/2010 | Park | A61F 2/1635 623/6.32 |
| 2010/0204790 A1* | 8/2010 | Whitsett | A61F 2/1694 623/6.39 |
| 2013/0304203 A1 | 11/2013 | Beer | |
| 2014/0172089 A1 | 6/2014 | Lee et al. | |

* cited by examiner

[Fig. 1]
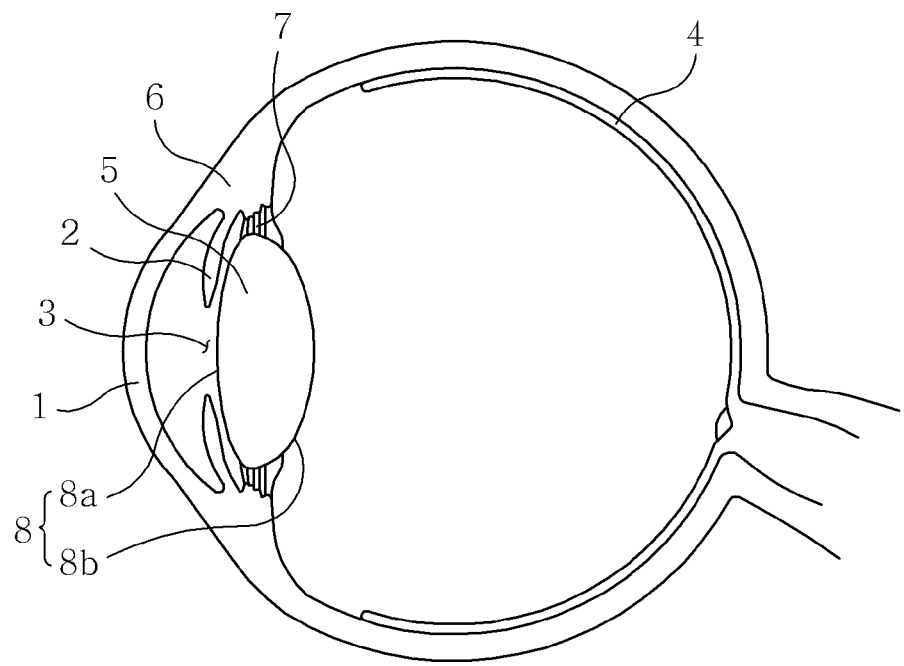
[Fig. 2]
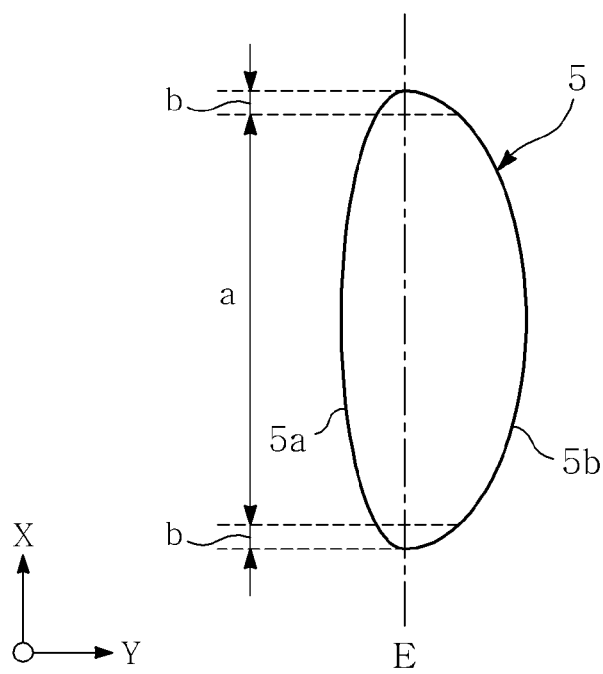

[Fig. 3]
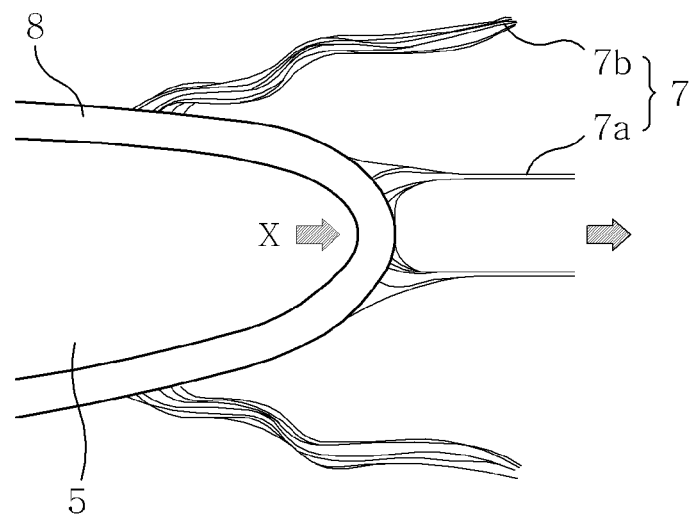
[Fig. 4]
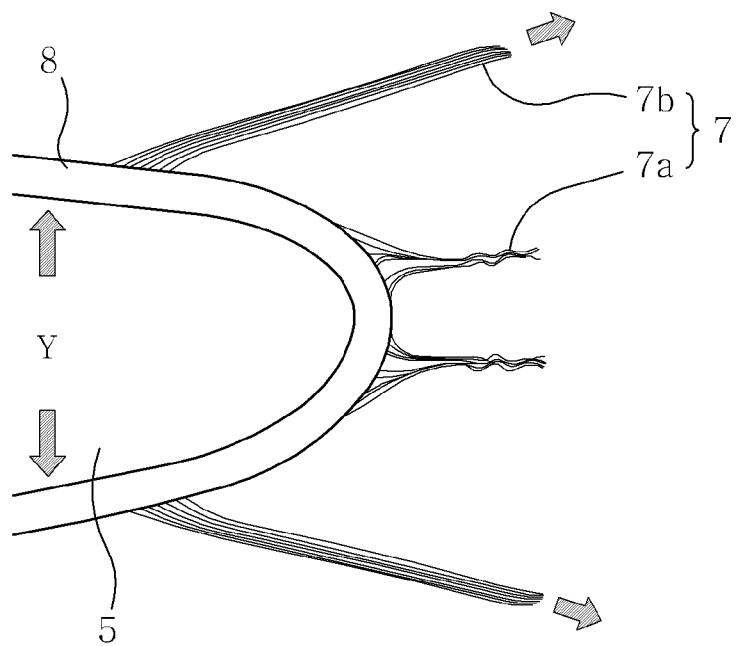

[Fig. 5]
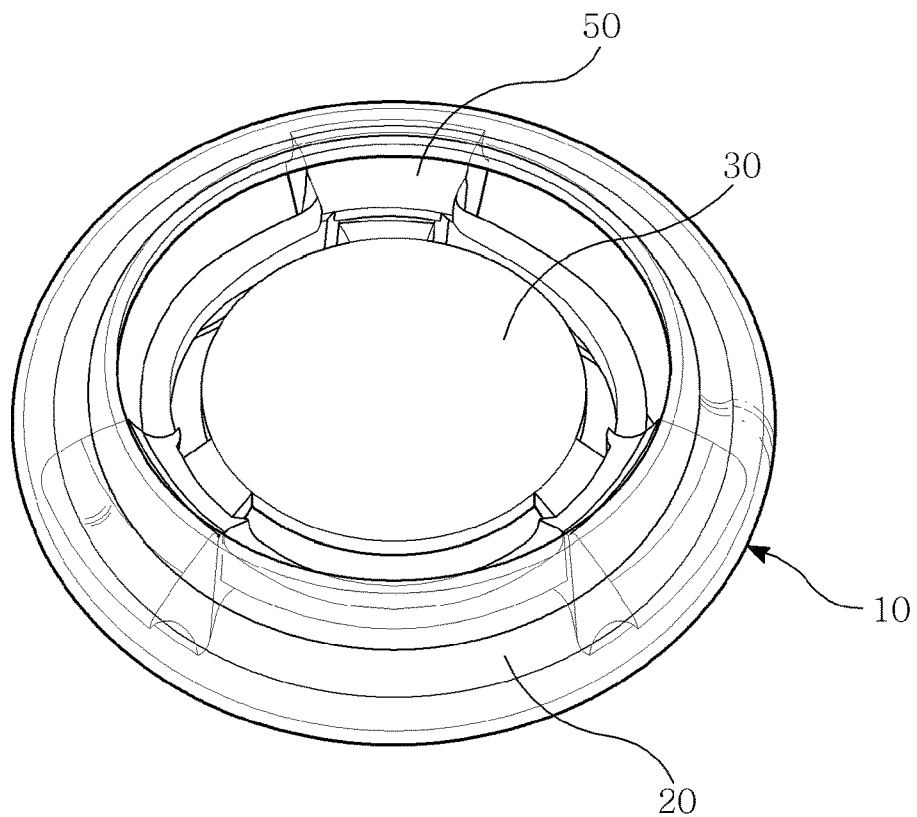
[Fig. 6]
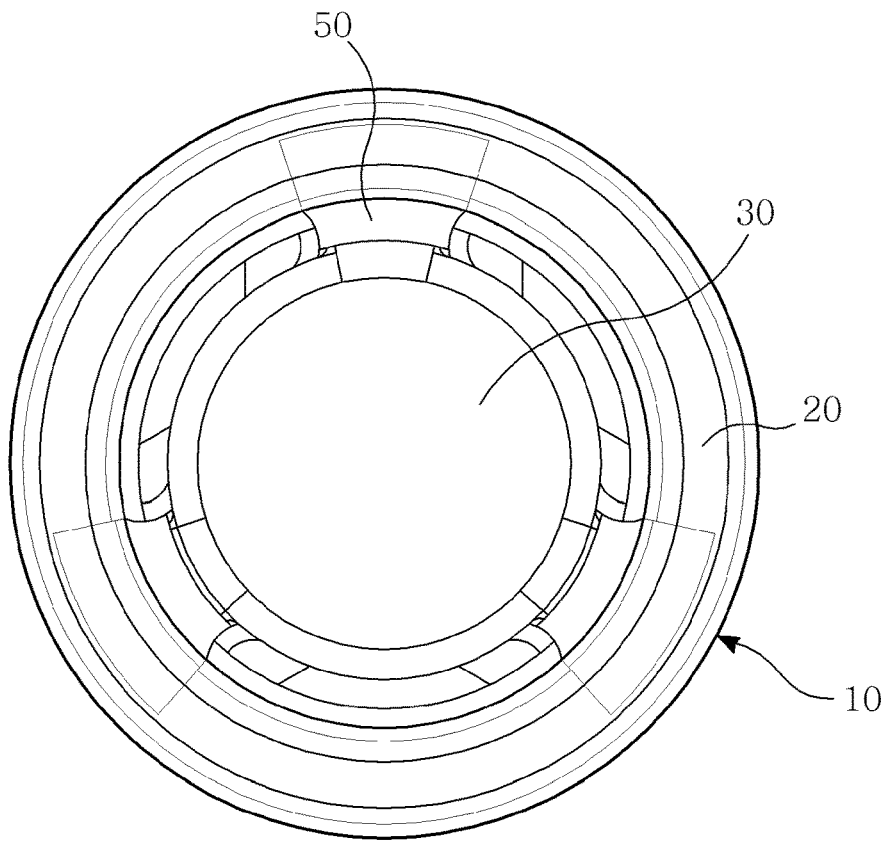

[Fig. 7]
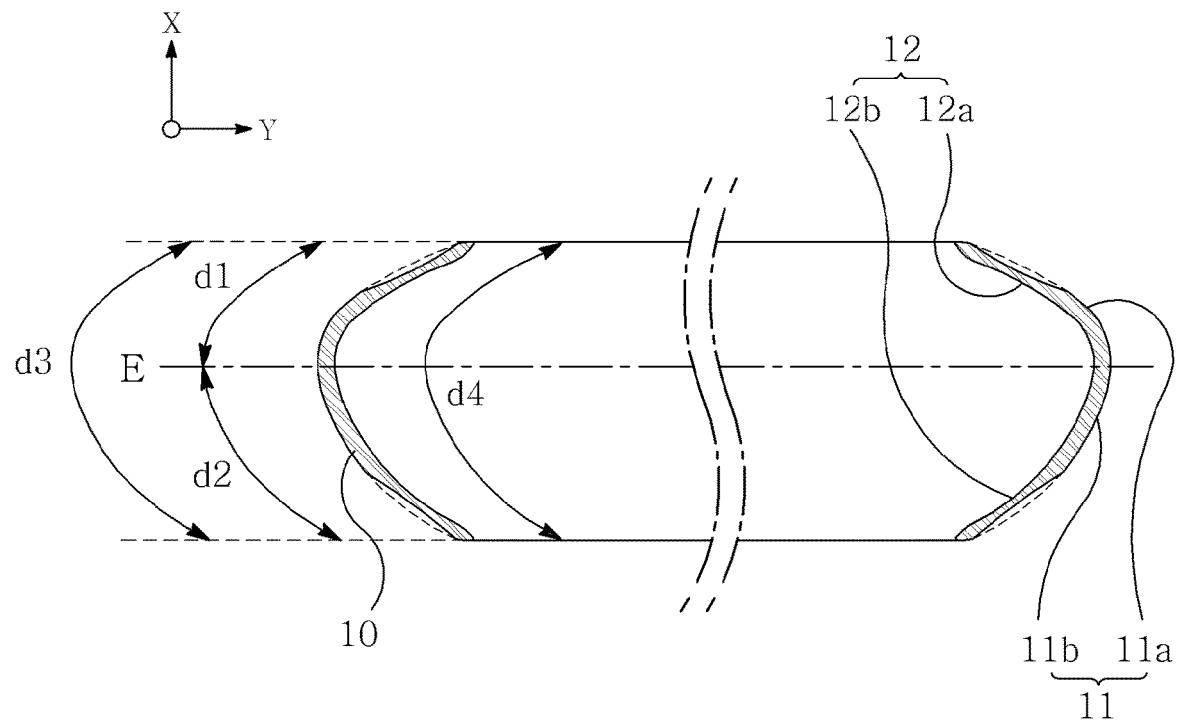
[Fig. 8]
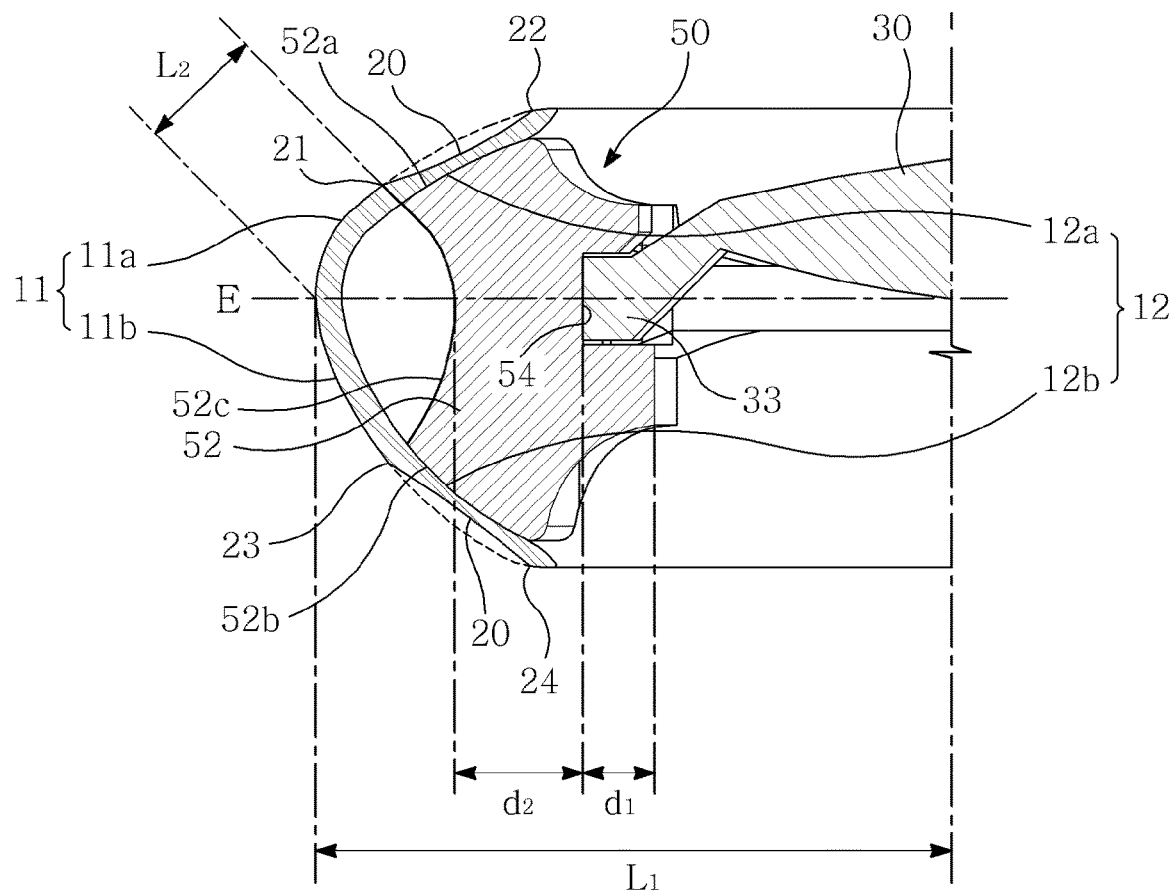

[Fig. 9]
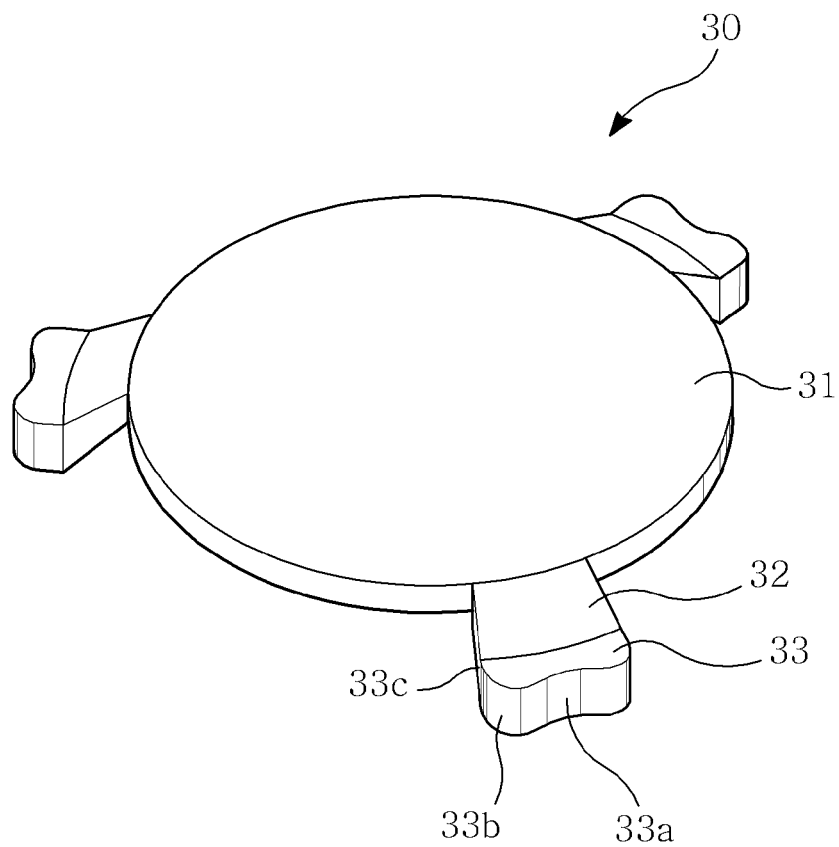
[Fig. 10]
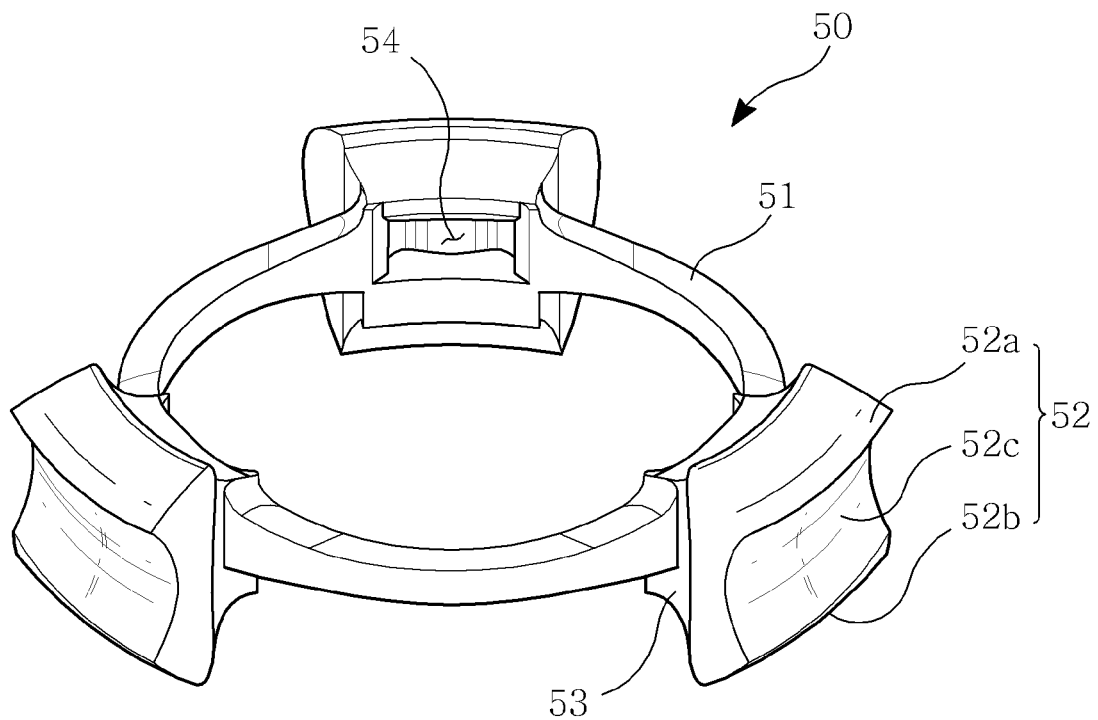

[Fig. 11]
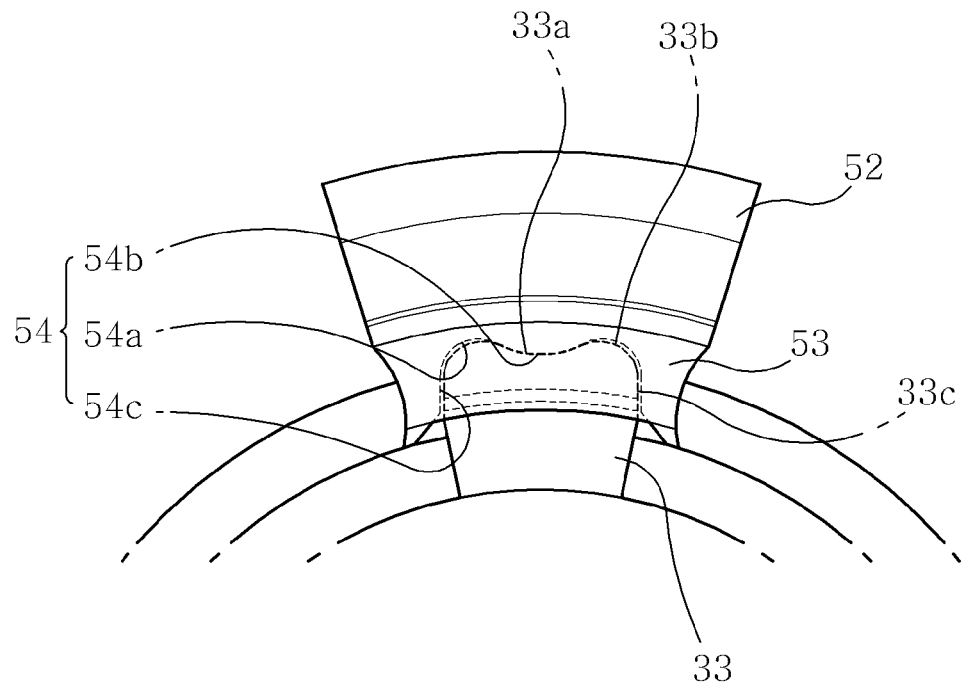
[Fig. 12]
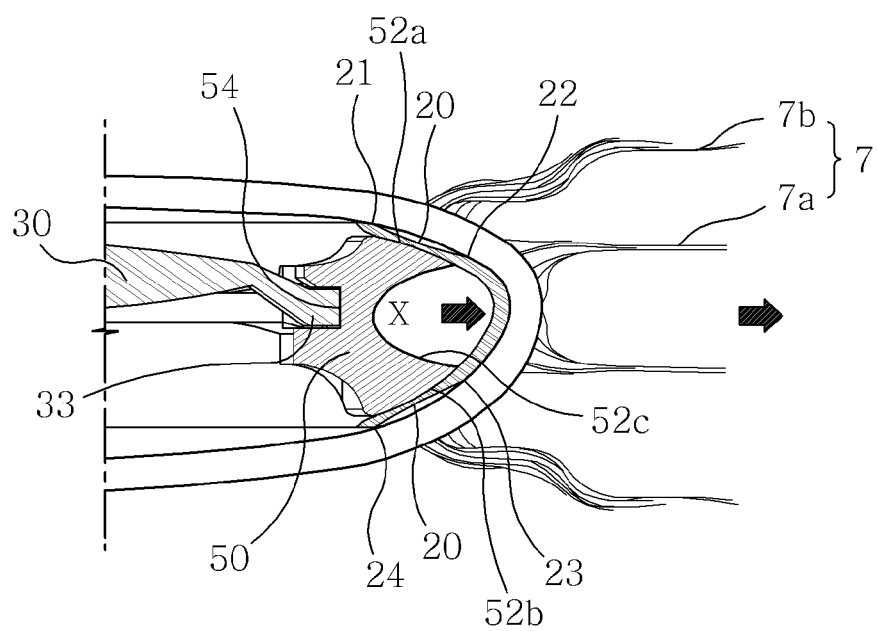

[Fig. 13]
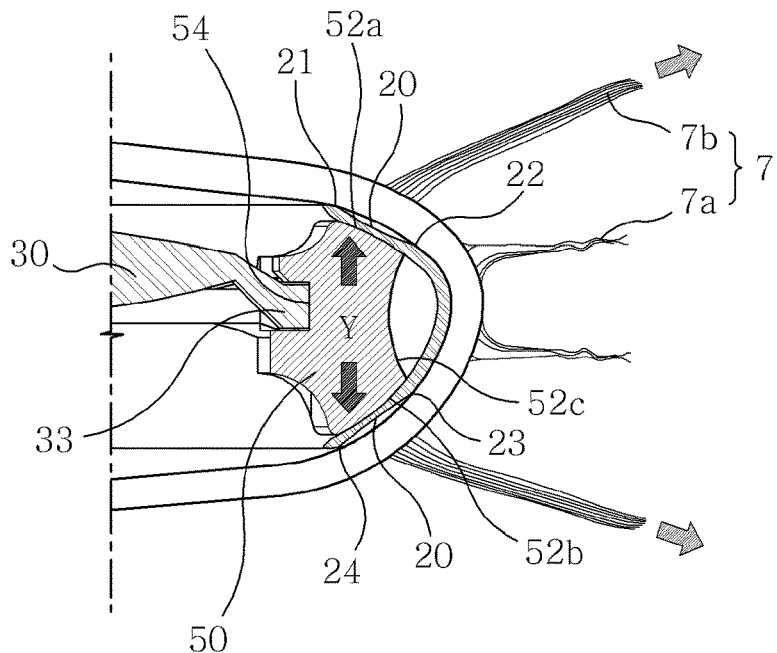
[Fig. 14]
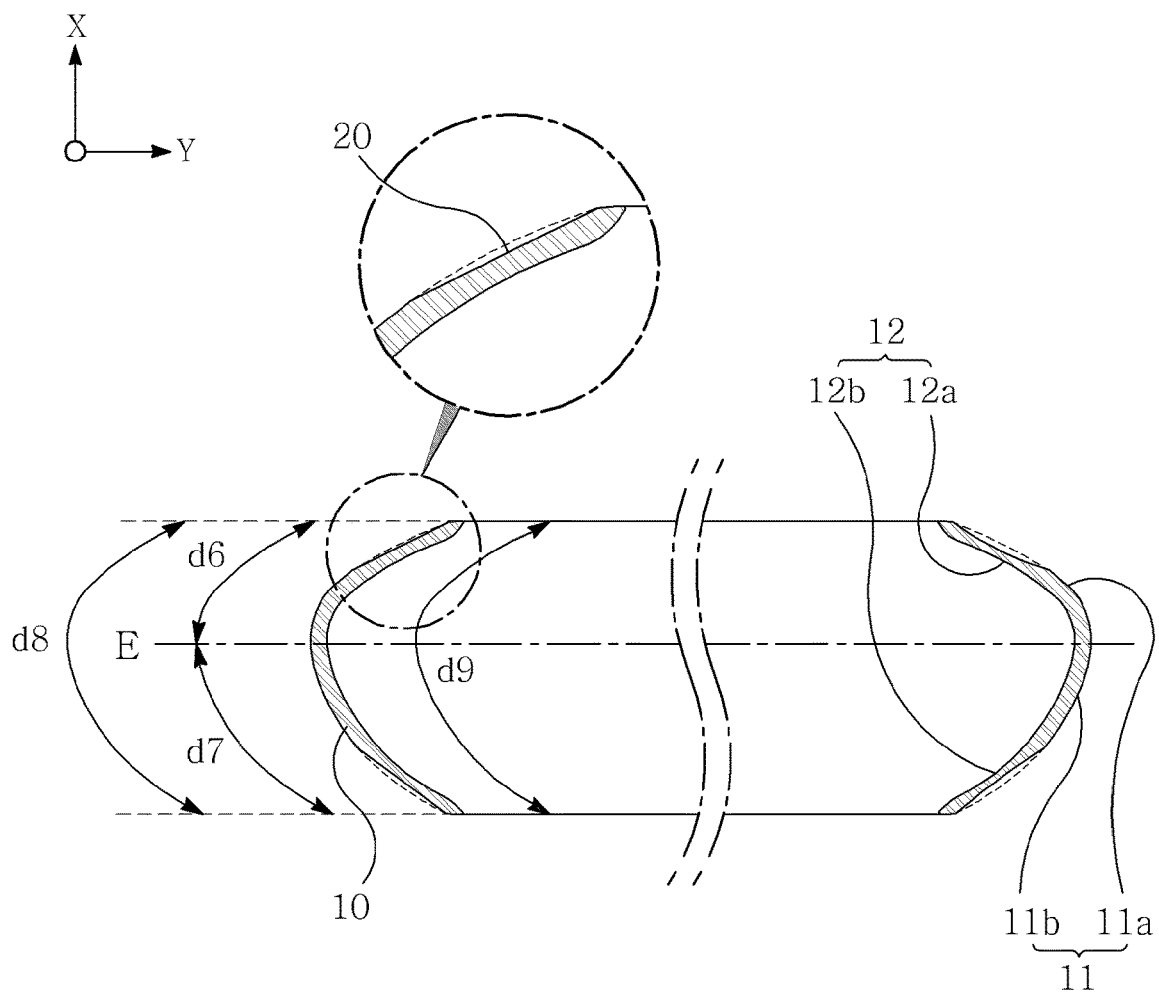

[Fig. 15]
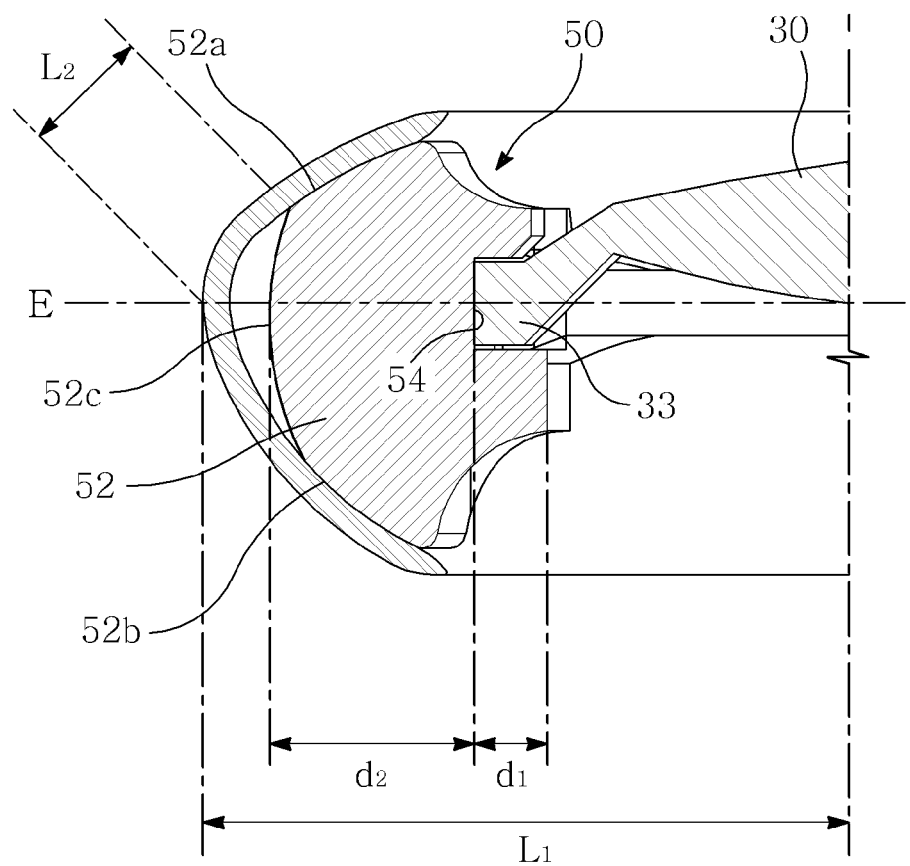

INTRAOCULAR LENS ASSEMBLY

CROSS-REFERENCE TO RELATED APPLICATIONS

The present specification is a U.S. National Stage of International Patent Application No. PCT/KR2015/005671, filed Jun. 5, 2015, which claims priority to and the benefit of Korean Patent Application No. 10-2015-0076716, filed May 29, 2015, the entire contents of which are incorporated herein by reference.

TECHNICAL FIELD

The present invention relates to an intraocular lens assembly. More particularly, the present invention relates to an intraocular lens assembly which improves the structure of an intraocular lens, the structures of a connection means and a support body supporting the intraocular lens so as to improve the location movement, and the contraction and expansion motilities of the intraocular lens.

BACKGROUND ART

In recent years, as one of treatment methods of ophthalmic diseases such as cataract that abnormalities in eye lenses, a method comprising steps of removing eye lens contents from a capsular sac and inserting an artificially produced intraocular lens into a space thereof have been increasingly used.

In the case of the insertion of the intraocular lens, the intraocular lens may give a clear sight to patients by replacing the natural eye lens. However, regardless of many advantages of the intraocular lens the intraocular lens has problems that a capsular sac which the intraocular lens is inserted into contracts after the insertion of the intraocular lens.

Accordingly, a new method has been increasingly used, comprising steps of inserting a capsular tension ring into an equatorial region of a capsular sac prior to the insertion of the intraocular lens and fixing the intraocular lens in the capsular tension ring.

The capsular tension ring, which is referred to as an open or a closed ring formations, is effective in partially relieving contraction of the capsular sac and fixing the intraocular lens.

In order to use the capsular tension ring more effectively, there have been recently studies to develop a structure for easily inserting the capsular tension ring, a structure for preventing a posterior capsule opacity, etc.

However, a serious problem in conventional intraocular lens implantation is that an anterior capsule and a posterior capsule of the capsular sac adhere to each other after the surgical operation, which leads to the loss of inherent function of contrail a thickness of an eye lens by relaxing and contracting Zonule of Zinn. That is, the problem is that a patient cannot be ensured sight through active three-dimensional movement of an intraocular lens in the direction of objects to be seen, but merely ensures a passive sight according to the predetermined power of an intraocular lens. Hereinafter, the problem will be described in detail with reference to the accompanying drawings, FIGS. 1 to 4.

FIG. 1 is a cross-sectional view showing a human eyeball and FIG. 2 is a cross-sectional view showing a structure of a natural eye lens. Referring to FIGS. 1 to 4, a cornea 1 is a transparent avascular tissue disposed in the outermost region of the eye and protects the eyeball. Also, the cornea serves to reflect the light together with the eye lens. An iris 2 functions as the iris of a camera by adjusting the intensity of the light entering the eye. In addition, a pupil 3 is a hole in the center of the iris 2, and adjusts the intensity of the light entering a retina 4 by contracting the hole under the bright light and expanding the hole under the dark light.

An eye lens 5 is a colorless and transparent avascular structure having a convex lens shape in both sides, and arranged in the back of the iris 2. The eye lens 5 is an organ that takes part in reflecting the light entering the eye together with the cornea 1, and a shape thereof is changed according to the contraction and relaxation of a ciliaris muscle 6 and a zonule of Zinn 7 coupled to the cilaris muscle 6.

Presbyopia is a state that the hardness of the eye lens 5 increases with the age, and therefore the shape of the eye lens 5 is not changed even if the ciliaris muscle 6 contracts, and the cataract is a disease that the eye lens 5 becomes opaque with the age.

The eye lens 5 is filled inside a capsular sac 8, and the capsular sac 8 is composed of an anterior capsule 8*a* and a posterior capsule 8*b*, each of which is in contact with an anterior surface 5*a* and a posterior surface 5*b* of the eye lens 5. At this time, the anterior surface 5*a* and the posterior surface 5*b* are coupled to each other in an equator E. Each of the anterior surface 5*a* and the posterior surface 5*b* is divided into a central region a and an equatorial region b according to the distance from the equator E. The central region a of the anterior surface 5*a* has a lesser curvature than the central region a of the posterior surface 5*b*, and the equatorial region b of the anterior surface 5*a* has a larger curvature than the equatorial region b of the posterior surface 5*b*.

The zonule of Zinn 7 is coupled along an edge of the capsular sac 8. The zonule of Zinn 7 is a fibrous tissue that couples the ciliaris muscle 6 and the capsular sac 8, and is composed of a first zonule portion 7*a* coupled to the center of the equatorial region in which the anterior capsule 8*a* and the posterior capsule 8*b* of the capsular sac 8 meets, and a second zonule portion 7*b* coupled to a circumference of the equatorial region.

FIGS. 3 and 4 are illustrative views showing an interaction of the zonule of Zinn, the eye lens, and the capsular sac when focused on a long distant and a short distance objects, respectively. In this specification, a Y-direction represents a visual axis direction of the eye lens, an X-direction represents an equatorial direction of the eye lens. The visual axis direction of the eye lens 5 means a direction that the light enters the eye lens 5 through the pupil, and the equatorial direction means a direction that, as a vertical direction of the visual axis direction, connects a point that the anterior capsule and the posterior capsule of the eye lens meets.

In the zonule of Zinn 7, the first zonule portion 7*a* coupled to the center of the equatorial region of the capsular sac 8 is pulled taut and the second zonule portion 7*b* coupled to the circumference of the equatorial region of the capsular sac 8 is relaxed when focused on the long distance object. As a result, the capsular sac 8 is extended in an X direction of the eye lens 5, and therefore the eye lens 5 arranged inside the capsular sac 8 is extended in the same direction.

In the zonule of Zinn 7, the first zonule portion 7*a* coupled to the center of the equatorial region of the capsular sac 8 is relaxed and the second zonule portion 7*b* coupled to the circumference of the equatorial region of the capsular sac 8 is pulled taut when focused on the short distance object. As a result, the capsular sac 8 as projected in a Y-direction of the eye lens and therefore eye lens 5 arranged inside the capsular sac 8 is extended in the same direction. As described above, the capsular sac 8 having a natural eye lens disposed therein is coupled to the zonule of Zinn 7, and takes part in deforming shapes of the natural eye lens actively, but when applying the conventional intraocular lens and capsular tension ring forces the capsular sac to contract, which leads the substantial loss of its functions.

In particular, the ciliaris muscle 6, which is coupled to the zonule of Zinn 7 to take part in the deformation of the eye lens 5, is intrinsic ocular muscle that maintains the endless function until a person dies. Therefore, the conventional method of artificially removing an ability of healthy ciliaris muscle 6 must be improved.

In addition, development of the intraocular lens assembly structure is needed when surgically inserting the intraocular lens, which the assembly transfers force generated by movement of the zonule of Zinn 7 to the intraocular lens effectively, thereby improving performance of the intraocular lens.

DISCLOSURE

Technical Problem

Accordingly, the present invention has been made keeping in mind the above problems occurring in the related art, and an object of the present invention is to provide an intraocular lens assembly which has improved movement transfer performance, capable of transferring a force applied by a zonule of Zinn to an intraocular lens.

In addition, another object of the present invention is to provide an intraocular lens assembly which transfers movement of a zonule of Zinn to an intraocular lens effectively, thereby improving performance of the intraocular lens.

Furthermore, a further object of the present invention is to provide an intraocular lens assembly which is configured to improve the structure of a coupling portion between a connection means and an intraocular lens so as to efficiently transfer complex movement of a zonule of Zinn to the intraocular lens.

Technical Solution

In order to accomplish the above and other objects, an intraocular lens assembly according to an embodiment of the present invention includes: an intraocular lens support body configured in a shape of a ring inserted into a capsular sac of an eyeball, an outer circumferential surface of the intraocular lens support body, which contacts the capsular sac, including a first front contact portion that contacts a front portion of the capsular sac and a first rear contact portion that contacts a rear portion of the capsular sac, and an inner circumferential surface of the intraocular lens support body, which faces the outer circumferential surface, including a second front contact portion that faces the first front contact portion and a second rear contact portion that faces the first rear contact portion; a connection means including a third front contact portion, which contacts at least one section of the second front contact portion, a third rear contact portion, which contacts at least one section of the second rear contact portion, and a deformation facilitating groove, which is provided between the third front contact portion and the third rear contact portion so as to form a space spaced apart from the inner circumferential surface; and an intraocular lens connected to the connection means.

The intraocular lens may be provided with a haptic portion radially protruding from an optic portion, and a groove, where the haptic portion is coupled, may be provided on an inner circumferential surface of the connection means.

An end of the haptic portion may be provided with a convex portion and a concave portion, and the groove may be provided with a concave portion having a cross section corresponding to the convex portion and a convex portion having a cross section corresponding to the concave portion.

The connection means may include: a ring portion configured as a ring shape; a mounting portion protruding from the ring portion radially; and an expanded portion protruding from the mounting portion to have an expanded cross section so as to come into tight contact with the inner circumferential surface of the intraocular lens support body, being provided with the deformation facilitating groove near a center region thereof, and being provided with the groove on an inner circumferential surface thereof.

A start point of the deformation facilitating groove of the connection means may be disposed at a position facing a point on the outer circumferential surface 11 where a rectilinear distance L2 from an equator to the point is 0.9 mm to 1.3 mm, and a distance from a lower surface of the groove to the deformation facilitating groove may be 0.4 mm to 1.1 mm.

The intraocular lens support body may provide a complex movement transfer surface recessed toward a central portion of the assembly on a part of the first front contact portion so as to improve movement transfer performance.

The complex movement transfer surface may be configured to have a rectilinear cross section when projecting in a front of a visual axis direction of the eye lens.

The complex movement transfer surface may be configured to have an arc-shaped cross section when projecting in a front of a visual axis direction of the eye lens.

The complex movement transfer surface may be disposed around the second zonule portion when the intraocular lens support body is disposed at the capsular sac.

The complex movement transfer surface formed on the first front contact portion may be disposed at a distance in a range of 0.9 mm to 1.5 mm apart from an equator.

The complex movement transfer surface formed on the first rear contact portion 11*b* may be disposed at a distance in a range of 1.2 mm to 1.9 mm apart from an equator.

The inner circumferential surface of the intraocular lens support body may be configured to be in a recessed cross section shape toward an equator, and the inner circumferential surface may include: the second front contact portion extending from the equator to an end of the first front contact portion and forming at least a part thereof as an arc shape; and the second rear contact portion extending from the equator to an end of the first rear contact portion and forming at least a part thereof as an arc shape.

Each arc of the first front contact portion, the first rear contact portion, the second front contact portion, and the second rear contact portion may be configured to be a part of an ellipse, and a length of a minor axis of the ellipse included in the arc of the first front contact portion may be shorter than the first rear contact portion thereof, and a length of a minor axis of the ellipse included in the arc of the second front contact portion may be shorter than the second rear contact portion thereof.

The length of the minor axis of the ellipse included in the arc of the second rear contact portion may be the longest and the length of the minor axis of the ellipse included in the arc of the first front contact portion may be the shortest.

A part of the first rear contact portion may further include the complex movement transfer surface recessed toward the central portion so as to improve movement transfer performance.

Advantageous Effects

As described above, the intraocular lens assembly according to the present invention can efficiently transfer complex movement due to force, which is generated from the ciliary muscle and transferred through the zonule of Zinn and the capsular sac, to the intraocular lens, thereby improving performance of the intraocular lens.

In addition, the intraocular lens assembly according to the present invention may be applied to an intraocular lens implantation treating cataract, presbyopia, high myopia, and so on. Also, the intraocular lens assembly may replace for a laser-assisted in situ keratomileusis (LASIK) and an implantable contact lens (ICL) operations.

Furthermore, the intraocular lens assembly according to the present invention includes the complex movement transfer surface recessed on the outer circumferential surface of the intraocular lens support body and the connection structure between the connection means and the intraocular lens is improved, such that the complex movement of the zonule of Zinn such as twisting and including the movement toward X-axis, Y-axis, and Z-axis directions is transferred to the intraocular lens accurately, thereby improving performance of the intraocular lens.

DESCRIPTION OF DRAWINGS

FIG. 1 is a cross-sectional view showing a human eyeball;

FIG. 2 is a cross-sectional view showing a structure of a natural eye lens;

FIG. 3 is an illustrative views showing interaction and movement of a zonule of Zinn and an eye lens when focused on a long distance object;

FIG. 4 is an illustrative views showing interaction and movement of a zonule of Zinn and an eye lens when focused on a short distance object;

FIG. 5 is a perspective view showing an intraocular lens assembly having an intraocular lens according to an embodiment of the present invention;

FIG. 6 is a plan view showing the intraocular lens assembly of FIG. 5;

FIG. 7 is a cross-sectional view showing the intraocular lens assembly of FIG. 5;

FIG. 8 is a cross-sectional view showing the intraocular lens assembly of FIG. 5 is assembled;

FIG. 9 is a perspective view showing the intraocular lens of FIG. 5;

FIG. 10 is a perspective view showing a connection means of FIG. 5;

FIG. 11 is a cross-sectional view showing a coupling portion of the intraocular lens of FIG. 5;

FIG. 12 is an illustrative view of an interaction and movement of a zonule of Zinn, an eye lens, an intraocular lens assembly when focused on a long distance object and assembled the intraocular lens assembly according to the embodiment of the present invention;

FIG. 13 is an illustrative view of an interaction and movement of a zonule of Zinn, an eye lens, an intraocular lens assembly when focused on a short distance object and assembled the intraocular lens assembly according to the embodiment of the present invention;

FIG. 14 is a cross-sectional view showing an intraocular lens support body according to an embodiment of the present invention;

FIG. 15 is a cross-sectional view showing a connection means according to an embodiment of the present invention.

BEST MODE

Hereinafter, an intraocular lens assembly according to an embodiment of the present invention will be described with reference to the accompanying drawings. The same reference numerals will be used throughout the drawings about the same or like elements or parts of the conventional structure, and detail description is referred to FIGS. 1 to 4.

1) As shapes, sizes, percentages, angles, numbers, etc. are roughly shown in the accompanying drawings, some variations thereof is allowed. 2) As the drawings are drafted from the observer's perspective, any direction or position to describe the drawings may be available for various modifications according to the observer's position. 3) The same reference numerals will be used on the same portions even in different drawings. 4) The terms "comprise", "have", "composed of", etc. may be interpreted to mean "any other portion can be added" unless "only" is used therewith. 5) Any element used in a singular form may also be interpreted to indicate plural forms. 6) Although shapes, comparisons in size, position relations, etc. are not described with "about", "substantially", etc., they may be interpreted to cover a general scope of tolerance. 7) Although the terms "after ~", "before ~", "subsequently", "following", "this time", etc., are used, they may not be used as a meaning to limit a temporal point. 8) The terms "first", "second", "third", etc. are used selectively, exchangeably, or repeatedly, and they are not interpreted as a limited meaning. 9) Where a position relation between two portions is described with "~ on", "on the upper part of ~", "on the lower part of ~", "beside ~", "on a side ~", etc., there may be at least one other portion between the two portions unless they are used with "immediately". 10) Where parts are electrically connected by using "or" between them, the parts may be interpreted to cover any combination thereof as well as respectively. Where the parts are electrically connected "~ or, one of ~", they are interpreted to mean the parts respectively.

FIG. 5 is a perspective view showing an intraocular lens assembly having an intraocular lens according to an embodiment of the present invention, FIG. 6 is a plan view showing the intraocular lens assembly of FIG. 5, FIG. 7 is a cross-sectional view showing the intraocular lens assembly of FIG. 5, FIG. 8 is a cross-sectional view showing the intraocular lens assembly of FIG. 5 is assembled, FIG. 9 is a perspective view showing the intraocular lens of FIG. 5, FIG. 10 is a perspective view showing a connection means of FIG. 5, FIG. 11 is a cross-sectional view showing a coupling portion of the intraocular lens of FIG. 5, FIG. 12 is an illustrative view of an interaction and movement of a zonule of Zinn, an eye lens, an intraocular lens assembly when focused on a long distance object and assembled the intraocular lens assembly according to the embodiment of the present invention, FIG. 13 is an illustrative view of an interaction and movement of a zonule of Zinn, an eye lens, an intraocular lens assembly when focused on a short distance object and assembled the intraocular lens assembly according to the embodiment of the present invention, FIG. 14 is a cross-sectional view showing an intraocular lens support body according to an embodiment of the present invention, and FIG. is a cross-sectional view showing a connection means according to an embodiment of the present invention.

Referring to FIGS. 5 to 8, the intraocular lens assembly having an intraocular lens support body 10 according to the embodiment of the present invention includes an intraocular lens 30, an intraocular lens support body 10 surrounding the intraocular lens 30, and a connection means 50 fixing the intraocular lens 30 to the intraocular lens support body 10. The connection means 50 holds the intraocular lens 30 inside thereof and is configured as structures inserted and mounted inside the intraocular lens support body 10.

The intraocular lens support body 10 is configured in a shape of a ring inserted into a capsular sac. It is preferable that the intraocular lens support body 10 is configured in a closed ring shape but an open ring shape is acceptable.

An outer circumferential surface 11 and an inner circumferential surface 12 of the intraocular lens support body 10 may be formed by different materials to enhance deformation performance according to movement of the zonule of Zinn.

An entire length of the outer circumferential surface 11 is configured to be longer than an entire length of the inner circumferential surface 12. It is preferable that an equator E is configured to be thickest and becomes thin toward each end.

A diameter of the intraocular lens support body 10 is almost same with an inner diameter of the capsular sac 8.

The diameter of the capsular sac 8 differs from people to people. Generally, the diameter is in a range of 9 mm to 13 mm. It is preferable that an equator diameter of the intraocular lens support body 10 is same with an inner equator diameter of a patient eye lens.

Materials of the intraocular lens support body 10 and the intraocular lens 30 may be composed of one or more than one selected from the group consisting of silicone, silicone elastomer, silicone polymer, polydimethyl siloxane, polypropylene, polyimide, polybutester, polymethyl methacrylate (PMMA), microplex PMMA, CQ-UV PMMA, acrylic resin, rigid acrylic, flexible acrylic, acrylate plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxyethyl methacrylate (2-HEMA), N-vinyl pyrrolidone (NVP), polyvinylpyrrolidone (PVP), methacrylic acid (MAA), glycerol methacrylate (GMA), dimethyl siloxane (DMS), polyhydroxyethyl methacrylate (PHEMA), poly HEMA hydrogel, poly HEMA hydrogel with UV absorption, silicone hydrogels, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, HEMA/PC, and so on.

As shown in FIG. 7, an outer circumferential surface 11 contacts at least one section of an inner surface of the capsular sac 8. The outer circumferential surface 11 includes a first front contact portion 11a and a first rear contact portion 11b divided by the equator E, which is an end protruding convexly. The first front contact portion 11a convexly protrudes toward one side and at least a part thereof forms an arc shape, and a first rear contact portion 11b convexly protrudes toward opposite side and at least a part thereof forms an arc shape. The first front contact portion 11a has a greater curvature than the first rear contact portion 11b thereof in a cross section when projecting in a front of a visual axis direction of the eye lens (Y-direction). This is to form the cross section like the equator cross section shape of a natural eye lens when projecting in the front of the outer circumferential surface 11, as described above, the anterior surface of the eye lens center portion has a lesser curvature than the posterior thereof but the curvature changes when close to the equatorial region.

Preferably, the outer circumferential surface 11 is configured to be same with a cross section shape of a patient inherent eye lens. A photograph of the cross section shape of the patient inherent eye lens before surgery is taken using ultrasonic imaging, CT, and MRI. The outer circumferential surface 11 has a cross section shape between mydriasis and miosis, but may have a shape that accord with the cross section shape of the eye lens having a pupil size of 3 mm to 4 mm. Therefore, the outer circumferential surface 11 accords with a shape of the inner surface in the equatorial region of the capsular sac 8.

As shown in FIG. 7, it is preferable that the outer circumferential surface 11 has a length in a range of to 3 times of a length of a region from an anterior second zonule portion 7b to a posterior second zonule portion 7b on an outer surface of the capsular sac 8 in a cross section when projecting in a front of a visual axis direction of the eye lens. In case that the outer circumferential surface 11 is formed in a shorter length than the times of the region between the second zonule portions 7b, force transferred to the intraocular lens 30 with the movement of the zonule of Zinn is not transferred effectively. On the other hand, in case that the outer circumferential surface 11 is formed in a longer length than the 3 times of the region between the second zonule portions 7b, the optic portion of the intraocular lens 30 may be covered. Therefore, the outer circumferential surface 11 may have a total length of 2 mm to 8 mm, following such range.

As shown in FIG. 7, an extended length d1 from the equator E to an end point of the first front contact portion 11a, and an extended length d2 from the equator E to an end point of the first rear contact portion 11b may be generally in a range from 1 mm to 4.2 mm in a cross section when projecting in a front of a visual axis direction of the eye lens. It is difficult to insert the intraocular lens support body 10 in the surgery and the optic portion is too small when the extended length exceeds 4.2 mm. On the other hand, the intraocular lens support body 10 is disposed at a more inner position than a point where the second zonule portion 7b of the zonule of Zinn is coupled to the capsular sac 8 when the extended length is less than 1 mm, and therefore, force transferred by the movement of the zonule of Zinn induced in the ciliaris muscle is not transferred to the intraocular lens 30 properly, which leads to in sufficient movement and deformation of the intraocular lens 30.

The extended length d1 from the equator E to the end point of the first front contact portion 11a may be different from the extended length d2 from the equator E to the end point of the first rear contact portion 11b. It is preferable that the extended length d2 is longer than the extended length d1.

The outer circumferential surface 11 is configured to be in a convexly protruding shape in a radial direction. A roughness of the intraocular lens support body 10 may be greater than other surface or a separate adhesive material may be added to facilitate mounting on the capsular sac. For example, a tissue glue or glue may be used as the adhesive material.

The inner circumferential surface 12 is configured to be in a recessed cross section shape toward the equator. The inner circumferential surface 12 includes a second front contact portion 12a extending from the equator E to the end of the first front contact portion 11a and forming at least a part thereof as an arc shape, and a second rear contact portion 12b extending from the equator E to the end of the first rear contact portion 11b and forming at least a part thereof as an arc shape. The inner circumferential surface 12 is a surface to which the connection means 50 is coupled.

A total extended length d4 of the inner circumferential surface 12 is configured to be shorter or equal to a total extended length d3 of the outer circumferential surface 11. This is for amplifying or maintaining force transferred to the outer circumferential surface 11 from the zonule of Zinn when the force is transferred to the inner circumferential surface 12.

Since the extended length d4 is shorter than the extended length d3, the movement and the deformation are more induced according to the movement of the outer circumferential surface 11. When force F1 is transferred to the outer circumferential surface 11 from the zonule of Zinn, force transferred to the inner circumferential surface 12 becomes F2 (=k*F1, k≥1). Here, k is a constant determined by a length ratio of the extended length d3 and the extended length d4. The length ratio of d3 and d4 may be varied according to the ability of the zonule of Zinn of the patient, a length of d4 is preferably longer as much as 0.4 to 1 times than a length of d3.

In addition, each arc of the first front contact portion 11a, the first rear contact portion 11b, the second front contact portion 12a, and the second rear contact portion 12b may be configured to be a part of an ellipse.

At this point, if each ellipse is located in a same axis and is controlled by magnifying to locate each vertex of a major axis in a same point, a length of a minor axis of the ellipse included in the arc of the first front contact portion 11a is shorter than the first rear contact portion 11b thereof, and a length of a minor axis of the ellipse included in the arc of the second front contact portion 12a is shorter than the second rear contact portion 12b thereof. In addition, among the minor axes, the minor axis of the ellipse included in the second rear contact portion 12b is the longest and the length of the minor axis of the ellipse included in the arc of the first front contact portion 11a is the shortest.

As shown in FIGS. 7 and 8, a complex movement transfer surface 20 is provided on the outer circumferential surface 11 of the intraocular lens support body 10. Each of the complex movement transfer surface 20 is formed on each part of the first front contact portion 11a and the first rear contact portion 11b. In addition, the complex movement transfer surface 20 is configured to be in a concave shape toward the center portion so as to improve movement transfer performance facilitating transfer of the movement of the zonule of Zinn (particularly, movement of the second zonule portion) to the intraocular lens 30. It is preferable that a cross section of the complex movement transfer surface 20 is configured to be in an arc-shaped cross section when projecting in a front of a visual axis direction of the eye lens. As shown in FIG. 14, the complex movement transfer surface 20 of the intraocular lens support body 10 according to an embodiment of the present invention may be configured to have a rectilinear cross section when projecting in a front of a visual axis direction of the eye lens. In addition, it is preferable that each of the complex movement transfer surface 20 configured to have the arc-shaped or the rectilinear cross section is located near each of the second zonule portion 7b included in the zonule of Zinn. However, the location of the complex movement transfer surface 20 is not limited near the second zonule portion 7b, but any location between the first zonule portion 7a and the second zonule portion 7b is acceptable for the complex movement transfer surface 20, and at this point, it is preferable that the complex movement transfer surface 20 is located to overlap the second zonule portion 7b partially. The intraocular lens support body 10 having the complex movement transfer surface 20 therein may be configured to form a reduced cross section of the complex movement transfer surface 20 toward an end as the complex movement transfer surface 20 is concavely formed.

It is preferable that the complex movement transfer surface 20 formed on the first front contact portion 11a is disposed at a distance in a range of 0.9 mm to 1.5 mm apart from the equator E. That is, it is preferable that a distance from a front start point 21 of the complex movement transfer surface 20 to the equator E is 0.9 mm, and a distance from a front end point 22 of the complex movement transfer surface 20 to the equator E is 1.5 mm.

It is preferable that the complex movement transfer surface 20 formed on the first rear contact portion 11b is disposed at a distance in a range of 1.2 mm to 1.9 mm apart from the equator E. That is, it is preferable that a distance from a rear start point 23 of the complex movement transfer surface 20 to the equator E is 1.2 mm, and a distance from a rear end point 24 of the complex movement transfer surface 20 to the equator E is 1.9 mm.

In addition, since the complex movement transfer surface 20 is configured to be in a concave shape on the outer circumferential surface configured to protrude convexly, the complex movement transfer surface 20 facilitates that the movement of the zonule of Zinn, applying to three axes, X-axis, Y-axis, and Z-axis, complexly at the same time and not only applying movement to one direction like X-axis or Y-axis, is transferred to the connection means 50 and the intraocular lens 30 effectively. The complex movement transfer surface 20 transfers the movement and volume change of the zonule of Zinn to the intraocular lens 30 in detail. That is, complex movement such as a delicate motion or twisting according to the movement of the zonule of Zinn is transferred to the connection means 50 and the intraocular lens 30 effectively through the complex movement transfer surface 20. In addition, the complex movement transfer surface 20 has a structural characteristic that a thickness of a position where the complex movement transfer surface 20 is formed is thinner than a side portion. Therefore, the deformation due to the movement of the zonule of Zinn is transferred smoothly. That is, the complex movement transfer surface 20 transfers the movement and deformation of the zonule of Zinn to the connection means 50 and the intraocular lens 30 easily.

As shown in FIGS. 5, 6, and 8, the intraocular lens 30 is coupled to the intraocular lens support body 10 by the connection means 50. The intraocular lens 30 maintains contacts with the inner circumferential surface 12 of the intraocular lens support body 10 and with the connection means 50, and a haptic portion 32 of the intraocular lens 30 is coupled to a groove 54 provided on an inner circumferential surface of the connection means 50. The intraocular lens 30 is disposed inside a ring of the connection means 50 and the connection means 50 is disposed inside a ring of the intraocular lens support body 10.

The intraocular lens 30 includes an optic portion 31 disposed in the rear of the pupil, and the haptic portion 32 protruding from the optic portion 31 radially and coupled to the inner circumferential surface of the connection means 50. The optic portion 31 of the intraocular lens 30 is an artificial lens inserted inwardly into the capsular sac, and is arranged in the rear of the pupil and functions as a lens of a natural eye lens in a hard lens, and it has a convex lens shape (but has a concave lens shape in some extremely myopic patients).

The intraocular lens 30 may be manufactured in various shapes and not particularly limited thereto. The haptic portion 32 is formed to be a plurality of branches protruding radially from a peripheral surface of the optic portion 31. Preferably, three haptic portions 32 are arranged at an interval of 120°. In addition, a ring-shaped support bar coupled to each end of the haptic portion 32 may be further provided. When the ring-shaped support bar coupled to each end of the haptic portion 32 is formed, the force transferring the movement of the zonule of Zinn is transferred to the intraocular lens 30 through the support bar and the haptic portion 32 effectively.

As shown FIG. 9, the haptic portion 32 protrudes to an opposite direction of the pupil when inserted in the eye ball. It is preferable that the haptic portion 32 is formed such that the protruding width thereof is longer than the protruding length thereof on the peripheral surface of the optic portion 31. Force such as twisting applying to the directions of the three axes may be transferred insufficiently if the protruding width is shorter than the protruding length, so the longer protruding width compared with the protruding length is important to improve movement transfer performance. In addition, it is preferable that the more protruding the haptic portion 32, the wider the width thereof. The end of the haptic portion 32 provides a fixing portion 33 protruding to be parallel with the optic portion 31. The fixing portion is a structure protruding slantingly to the opposite direction of the pupil based on a plane of optic portion 31 such that location of the optic portion 31 is changed following the pupil smoothly with less power. The protruding end of the fixing portion 33 is provided with a concave portion 33a and convex portion 33b repeated sequentially. As shown in FIG. 9, it is preferable that the fixing portion 33 is formed such that the concave portion 33a is disposed at the central region thereof and the convex portions 33b are disposed at both sides of the concave portion 33a. Each side portion 33c contacting to each of the convex portion 33b is configured to be in a round shape. Not shown but the side portion 33c may include a concave portion and a convex portion. The fixing portion 33 including the concave portion 33a and the convex portion 33b is disposed at the end of the haptic portion 32 such that the movement transfer performance transferring force applying to X-axis, Y-axis, and Z-axis is improved. That is, if the concave portion 33b and the convex portion 33a are not provided, slip occurs at a contact point of the fixing portion 33 and the groove 54 and power loss may be generated. Therefore, providing the concave portion 33a and the convex portion 33b prevents slipping thereby improving the movement transfer performance.

The connection means 50 includes a ring portion 51 configured as a ring shape, a mounting portion 53 protruding from the ring portion 51 radially, and an expanded portion 52 protruding from the mounting portion 53 to have an expanded cross section so as to come into tight contact with the inner circumferential surface 12 of the intraocular lens support body 10. The intraocular lens 30 is assembled to be disposed inside of the ring portion 51. Inside the expanded portion 52 is provided with the groove 54 where the fixing portion 33 is inserted into. The groove 54 has an inner surface corresponding to a shape of an outer circumference of the fixing portion 33. That is, the groove 54 includes a side portion 54c coming into tight contact with the side portion 33c of the fixing portion 33, a concave portion 54a coming into tight contact with the convex portion 33b, and a convex portion 54b coming into tight contact with the concave portion 33a. As described above, the fixing portion 33 and the groove 54 includes the concave and convex structures corresponding to each other and coming into tight contact each other, and the structures prevent slipping thereby improving the movement transfer performance.

The expanded portion 52 includes a third front contact portion 52a having a cross section corresponding to the second front contact portion 12a of the inner circumferential surface 12, a third rear contact portion 52b having a cross section corresponding to the second rear contact portion 12b of the inner circumferential surface 12, and a deformation facilitating groove 52c configured to be recessed in a predetermined depth on a central region encountered the third front contact portion 52a and the third rear contact portion 52b. An upper surface and a lower surface of the mounting portion 53 configured to be in a round-shaped cross section toward both ends of the expanded portion 52. The inner circumferential surface 12 of the intraocular lens support body 10 comes into tight contact with peripheries of the expanded portion 52 such that the movement transfer performance is improved.

As shown in FIG. 8, a front portion and a rear portion of the deformation facilitating grooves 52c on the basis of position of the equator may be configured to have same curvatures, or may be configured to have different curvatures as curvatures of the third front contact portion 52a and the third rear contact portion 52b. A structure that curvatures of the front portion and the rear portion of the deformation facilitating grooves 52c are configured to be different each other is similar with a structure that the curvatures of the first front contact portion 11a and the first rear contact portion 11b are configured to be different each other.

As shown in FIG. 8, the deformation facilitating groove 52c may be configured to be in the recessed shape toward the central portion, or may be configured to be in a protruding shape toward the outer circumferential surface. On the basis of the position of the equator E, a start point of the deformation facilitating groove 52c is disposed collinearly with a point where the second zonule of Zinn 7b included in the zonule of Zinn 7 is disposed. That is, preferably, a position facing a point on the outer circumferential surface 11 where a rectilinear distance L2 is 1.1 mm from the equator is the start point of the deformation facilitating groove 52c, but the rectilinear distance L2 may have a length in a range of 1.1 mm±0.2 mm according to a length of a diameter L. As deformation amount of the connection means 50 is increased by the deformation facilitating groove 52c, force transferred to the intraocular lens support body 10 from the zonule of Zinn is transferred to the intraocular lens 30 effectively. That is, as shown in FIGS. 12 and 13, the connection means 50 can be compressed and deformed in X-axis direction, and expanded and deformed in Y-axis direction by the deformation facilitating groove 52c smoothly. That is, the expanded portion 52 of the connection means 50 is easily deformed by a space generated due to the deformation facilitating groove 52c.

In addition, it is preferable that a depth of the groove 54 depressed to the inner circumferential surface of the connection means 50 is about 0.55 mm, but the depth of the groove 54 may have a length in a range of 0.55 mm±0.2 mm according to the length of the diameter L1.

In addition, a distance d2 from a lower surface of the groove 54 to the deformation facilitating groove 52c may have a length in a range of 0.4 mm to 1.1 mm according to the length of the diameter L1.

If the diameter of the connection means 50 is changed, the depth d1 and the rectilinear distance L2 are needed to ensure the lengths thereof. Therefore, as shown in FIG. 8, the deformation facilitating groove 52c may be configured to be in a recessed shape toward the central portion, or may be configured to be in a protruding shape toward the outer circumferential surface as shown in FIG. 15. As an example, the curvature of the deformation facilitating groove 52c is almost rectilinear when the diameter L1 of the connection means 50 is 9.8 mm. When the diameter L1 of the connection means 50 is equal to or longer than 9.8 mm, the deformation facilitating groove 52c is configured to be recessed toward the central portion as shown in FIG. 8. On the other hand, when the diameter L1 of the connection means is equal to or less than 9.8 mm, the deformation facilitating groove 52c is configured to be protruding toward the outer circumferential surface on the basis of a rectilinear as shown in FIG. 15. It is determined that the deformation facilitating groove 52c is configured to be recessed toward the central portion or configured to be protruding toward the outer circumferential surface to maintain the rectilinear distance L2 to be about 1.1 mm and the depth d1 to be 0.55 mm. This is because too short distance d2 may hurt eye lens, on the other hand, if the distance d2 is too long, the deformation may not be smoothly transferred. In addition, as shown in FIG. 15, when using the connection means 50 provided with the deformation facilitating groove 52c and coupled with the intraocular lens support body 10 not provided with the complex movement transfer surface 20, the movement of the zonule of Zinn is smoothly transferred to the intraocular lens 30 through the intraocular lens support body 10 and the connection means 50 by the deformation facilitating groove 52c. Likewise, when using the intraocular lens support body 10 provided with the complex movement transfer surface 20 and coupled with connection means 50 not provided with the deformation facilitating groove 52c, the movement of the zonule of Zinn is smoothly transferred to the intraocular lens 30 through the intraocular lens support body 10 and the connection means 50 by the complex movement transfer surface 20. It is preferable to use combination of the intraocular lens support body 10 provided with the complex movement transfer surface 20 and the connection means 50 provided with the deformation facilitating groove 52c so as to transfer the movement of the zonule of Zinn to the intraocular lens 30 smoothly.

A gap between the connection means 50 and the intraocular lens support body 10 generated by the deformation facilitating groove 52c is filled with aqueous humor (tear in the eye produced by ciliary body) in the eyeball.

Hereinafter, an interaction of the intraocular lens assembly according to the embodiment of the present invention will be described in detail with reference to the accompanying drawings.

As shown in FIG. 12, when focused on a long distance object, the first zonule portion 7a of the capsular sac 8 is pulled taut and the second zonule portion 7b is relaxed. Therefore, the equatorial region of the capsular sac 8 is subject to force generated when extended in an X-direction, and the intraocular lens 30 with elasticity disposed inside of the capsular sac 8 is also extended in the same direction, which leads to a thinner thickness of the intraocular lens 30 or location movement. At this point, the force applied by the zonule of Zinn 7 is not applied to only one direction of X-axis, but actually the force is complex movement combined directions of three axes, which are X-axis, Y-axis, and Z-axis. When such complex movement (including twisting) is transferred to the expanded portion 52 of the connection means 50 through the complex movement transfer surface 20 effectively, the connection means 50 has increased deformation amount by the deformation facilitating groove 52c provided on the connection means 50. And then the complex movement (including twisting) is transferred to the optic portion 31 of intraocular lens 30 through the groove 54, the fixing portion 33, and the haptic portion 32. At this point, functions of the complex movement transfer surface 20, the deformation facilitating groove 52c, the inner circumferential surface 12, the expanded portion 52, the groove 54, and the fixing portion 33 are described above.

As shown in FIG. 13, when focused on a short distance object, the first zonule portion 7a of the capsular sac 8 is relaxed and the second zonule portion 7b is pulled taut. Therefore, the equatorial region of the capsular sac 8 is protruded in a Y-direction, and the intraocular lens 30 with elasticity disposed inside the capsular sac 8 is also extended in the same direction, which leads to a thicker thickness of the intraocular lens 30 or location movement. At this point, the force applied by the zonule of Zinn 7 is not applied to only one direction of Y-axis, but actually the force is complex movement combined directions of three axes, which are X-axis, Y-axis, and Z-axis. When such complex movement (including twisting) is transferred to the expanded portion 52 of the connection means 50 through the complex movement transfer surface 20 effectively, the connection means has increased deformation amount by the deformation facilitating groove 52c provided on the connection means 50. And then the complex movement (including twisting) is transferred to the optic portion 31 of intraocular lens 30 through the groove 54, the fixing portion 33, and the haptic portion 32. At this point, functions of the complex movement transfer surface 20, the deformation facilitating groove 52c, the inner circumferential surface 12, the expanded portion 52, the groove 54, and the fixing portion 33 are described above.

As described above, the intraocular lens assembly according to the present invention is configured to have a structure including the fixing portion 33 provided with the concave portion 33a and the convex portion 33b disposed at the end of the haptic portion 32, and the groove 54 included in the connection means 50 and provided with the convex portion 54b and the concave portion 54a each corresponding to the cross sections of the concave portion 33a and the convex portion 33b of the fixing portion 33. The fixing portion 33 is mounted on the groove 54 such that improves the movement transfer performance. In addition, the expanded portion 52 of the connection means 50 is configured to be in a structure coming into tight contact with the inner circumferential surface 12 of the intraocular lens support body 10 such that improves the movement transfer performance. Furthermore, the deformation facilitating groove 52c is provided such that improves the movement transfer performance of the connection means 50.

In addition, when the intraocular lens support body 10 according to the present invention is provided with the complex movement transfer surface 20, the delicate movement or the complex movement applying to three axes direction of the zonule of Zinn is transferred to the connection means 50 and the intraocular lens 30 through the intraocular lens support body 10 effectively such that the thickness and the location of the intraocular lens 30 is capable of being controlled as the natural eye lens. That is, as the thickness of the natural eye lens is controlled by the interaction of the capsular sac coupled to the zonule of Zinn minutely, the deformation such as thickness change and location movement of the intraocular lens provided with the intraocular lens support body according to the present invention is also capable of being controlled.

While the present invention has been described in connection with the specific embodiments illustrated in the drawings, they are merely illustrative, and the invention is not limited to these embodiments. It is to be understood that various equivalent modifications and variations of the embodiments can be made by a person having an ordinary skill in the art without departing from the spirit and scope of the present invention. Therefore, the true technical scope of the present invention should not be defined by the above-mentioned embodiments but should be defined by the appended claims and equivalents thereof.

The invention claimed is:

1. An intraocular lens assembly, the assembly comprising:
an intraocular lens support body having a shape of a ring, an outer circumferential surface of the intraocular lens support body including a first front contact portion and a first rear contact portion, an inner circumferential surface of the intraocular lens support body facing the outer circumferential surface and including a second front contact portion and a second rear contact portion, the second front contact portion facing the first front contact portion and the second rear contact portion facing the first rear contact portion;
a connector including a third front contact portion that contacts a section of the second front contact portion, and a third rear contact portion that contacts a section of the second rear contact portion, the connector having a first groove that is configured to be recessed toward a central portion of the assembly on a central region, the first groove being disposed between the third front contact portion and the third rear contact portion, a space in the first groove spacing the connector apart from the inner circumferential surface; and
an intraocular lens connected to the connector,
wherein the intraocular lens support body is configured to be disposed in a capsular sac of an eyeball, and the outer circumferential surface of the intraocular lens support body is configured to contact the capsular sac, and
wherein the third front contact portion and the third rear contact portion are disposed on opposite sides with respect to an equator of the capsular sac.

2. The intraocular lens assembly of claim 1, wherein the intraocular lens includes:
an optic portion; and
a haptic portion radially protruding from the optic portion, wherein the haptic portion is coupled to a second groove provided on an inner circumferential surface of the connector.

3. The intraocular lens assembly of claim 2, wherein an end of the haptic portion includes a convex portion and a concave portion, and
wherein the second groove has a concave portion corresponding to the convex portion of the haptic portion, and a convex portion corresponding to the concave portion of the haptic portion.

4. The intraocular lens assembly of claim 3, wherein the connector includes:
a ring portion having a ring shape;
a mounting portion radially protruding from the ring portion; and
an expanded portion protruding from the mounting portion and in conformal contact with the inner circumferential surface of the intraocular lens support body, the first groove being provided on a center region of the expanded portion, the second groove being provided on an inner circumferential surface of the expanded portion.

5. The intraocular lens assembly of claim 2, wherein a start point of the first groove of the connector is disposed at a position facing a point on the outer circumferential surface of the intraocular lens support body, a rectilinear distance from the equator to the point being 0.9 mm to 1.3 mm,
wherein a distance from a lower surface of the second groove to the first groove is 0.4 mm to 1.1 mm.

6. The intraocular lens assembly of claim 1, wherein the intraocular lens support body has a complex movement transfer surface that is recessed toward the central portion of the assembly on a part of the first front contact portion, and
wherein the complex movement transfer surface is configured to be in a concave shape on the outer circumferential surface configured to protrude convexly, and a portion of the complex movement transfer surface contacts the capsular sac.

7. The intraocular lens assembly of claim 6, wherein the complex movement transfer surface is rectilinear.

8. The intraocular lens assembly of claim 6, wherein the complex movement transfer surface is arc-shaped.

9. The intraocular lens assembly of claim 6, wherein the complex movement transfer surface is configured to be disposed around a zonule portion when the intraocular lens support body is disposed in the capsular sac.

10. The intraocular lens assembly of claim 9, wherein the complex movement transfer surface is disposed at a distance in a range of 0.9 mm to 1.5 mm apart from the equator.

11. The intraocular lens assembly of claim 9, wherein the complex movement transfer surface is disposed at a distance in a range of 1.2 mm to 1.9 mm apart from the equator.

12. The intraocular lens assembly of claim 6, wherein the inner circumferential surface of the intraocular lens support body is recessed toward the equator,
wherein the second front contact portion extends from the equator to an end of the first front contact portion, a part of the second front contact portion having an arc shape, and
wherein the second rear contact portion extends from the equator to an end of the first rear contact portion, a part of the second rear contact portion having an arc shape.

13. The intraocular lens assembly of claim 12, wherein each of the first front contact portion and the first rear contact portion convexly protrudes toward one side and at least a part of each of the first front contact portion and the first rear contact portion forms an arc shape, and
wherein each arc shape of the first front contact portion, the first rear contact portion, the second front contact portion, and the second rear contact portion is part of an ellipse, a length of a first component of a minor axis of the ellipse including the arc shape of the first front contact portion being shorter than the first rear contact portion, and a length of a second component of the minor axis of the ellipse including the arc of the second front contact portion being shorter than the second rear contact portion.

14. The intraocular lens assembly of claim 13, wherein a length of a third component of the minor axis of the ellipse including the arc of the second rear contact portion being longer than the lengths of the first and the second components, and
wherein the length of the first component of the minor axis of the ellipse being shorter than the lengths of the second and the third components.

15. The intraocular lens assembly of claim 6, wherein the complex movement transfer surface is recessed toward the central portion.

16. The intraocular lens assembly of claim 1, wherein the first groove has a concave surface by being recessed toward a radially inward direction of the intraocular lens support body.

17. The intraocular lens assembly of claim 1, wherein the central region is adjacent to the third front contact portion and the third rear contact portion of the connector.

* * * * *